(12) United States Patent
Wortrich et al.

(10) Patent No.: US 6,592,543 B1
(45) Date of Patent: Jul. 15, 2003

(54) FLUID FLOW REGULATOR FOR A SMOKE EVACUATION SYSTEM AND METHOD OF USING SAME

(75) Inventors: Theodore S. Wortrich, Newport Coast, CA (US); Armand Maaskamp, Mission Viejo, CA (US); Michael Ekinaka, Irvine, CA (US)

(73) Assignee: Surgin Inc., Tustin, CA (US)

( * ) Notice: Subject to any disclaimer, the term of this patent is extended or adjusted under 35 U.S.C. 154(b) by 0 days.

(21) Appl. No.: 10/116,467

(22) Filed: Apr. 3, 2002

(51) Int. Cl.[7] .............................................. A61M 1/00
(52) U.S. Cl. ............................ 604/35; 95/284; 55/414
(58) Field of Search .............................. 604/35; 95/273, 95/286, 284; 55/410, 413–415

(56) References Cited

U.S. PATENT DOCUMENTS

| | | | |
|---|---|---|---|
| 4,874,513 A | | 10/1989 | Chakraborty et al. |
| 5,336,169 A | | 8/1994 | Divilio et al. |
| 5,451,222 A | * | 9/1995 | De Maagd et al. ........... 606/41 |
| 5,578,000 A | | 11/1996 | Greff et al. |
| 5,688,256 A | * | 11/1997 | Surratt et al. ............... 604/355 |
| 6,110,259 A | | 8/2000 | Schultz et al. |

OTHER PUBLICATIONS

PCT application No. PCT/US99/28204, International publication No. WO 00/32296, "Filter for use in Medical Procedures," by Charles S. Booth.

Surgical Smoke Clinical Update, [online]. Pall Medical Corporation [retrieved on Apr. 3, 2002]. Retrieved from the internet: <URL: http://www.pall.com/applicat/medical/laparoshield/SSmoke.pdf>.

Laparoshield ([TM])Laparoscopic Smoke Filtration System [online]. Pall Medical Corporation [retrieved on Apr. 3, 2002] Retrieved from the Internet <URL: http://www.pall.com/applicat/medical/laparoshield/Laparoshield.ds.pdf>.

* cited by examiner

Primary Examiner—Brian L. Casler
Assistant Examiner—Jeremy Thissell
(74) Attorney, Agent, or Firm—Michael Hoffman; The Soni Law Firm (57) ABSTRACT

A fluid flow regulator of a smoke evacuation system for use with laparoscopic and endoscopic surgery is disclosed. The fluid flow regulator is comprised of a flow regulating means and a conduit connecting means. The flow regulating means in one embodiment includes a diaphragm and one or more orifices of predetermined diameter to provide a significant obstruction to the flow of fluid through the evacuation system. When operatively coupled to the pressurized surgical site, the fluid flow regulator makes possible the continuous evacuation of surgical smoke while simultaneously maintaining the pneumoperitoneum in a distended position for the duration of the laparoscopic procedure. Also disclosed is a method of using the fluid flow regulator to continually evacuate surgical smoke in the course of laparoscopic and endoscopic surgical procedures without deflating the pneumoperitoneum, which hereto for has been used by prior art systems to evacuate surgical smoke.

20 Claims, 7 Drawing Sheets

FLUID FLOW REGULATOR FOR A SMOKE EVACUATION SYSTEM AND METHOD OF USING SAME

BACKGROUND

The present invention pertains to the field of the regulation of fluid being expelled from a surgical site. More particularly, the invention relates to a fluid flow regulator, which when used, regulates the flow of fluid from the surgical site and serves as a passive smoke evacuation system for a pressurized surgical site.

Minimally-invasive surgical procedures such as laparoscopic or endoscopic surgery have become increasingly common due to the fact that the procedures generally result in shorter recovery times, less side effects including secondary infections, shorter operating durations, and reduced costs. The term "endoscopic" as used herein encompasses arthroscopic, laparoscopic, hysteroscopic, thoracoscopic or any other similar closed surgical procedures performed with instruments inserted through small, artificially created openings or portals in the patient.

In conventional laparoscopic procedures, a first minimally-invasive surgery access port is formed in the patient's abdomen using a Veress needle to puncture the lapra or abdomen. An insufflator gas such as carbon dioxide is injected into the abdomen to distend the pneumoperitoneum, thereby creating an air space or cavity in proximity to the organs on which the surgical operation is to be performed. The cavity provides the work space necessary for the surgeon to maneuver the surgical instruments and endoscope, which are typically introduced into the surgical site through other access ports created by the surgeon.

The insufflation gas is forced into the surgical site such as the abdominal cavity under pressure by an insufflation device. A number of insufflation devices have two modes of operation, initiation mode and maintenance mode. The initiation mode pumps gas at a high rate in order to quickly distend the pneumoperitoneum. In the maintenance mode, the insufflation gas is pumped at a rate up to a maximum pressure to replace the amount of gas lost during the procedure. Many insufflation devices are capable of delivering a maximum flow rate of approximately 16 to 25 liters per minute.

The maintenance pressure held at the surgical site by the insufflation device will vary depending on the insufflation gas and the patient's weight for example. An obese patient will require a higher abdominal pressure in order to distend the pneumoperitoneum the same distance as that of a thinner patient.

Immediately after the pneumoperitoneum is first distended, an endoscope coupled to a television monitor is inserted into the abdominal cavity to visualize the interior of the surgical entry. In the case that the insertion of the trocar penetrates or punctures a major blood vessel, medical intervention including conventional invasive surgery may be required to control the hemorrhaging.

In the absence of exigent circumstances, the endoscope remains in the portal which is conventionally dedicated for that instrument. Additional portals are created to provide access for other surgical instruments including probes and other surgical devices that are individually inserted through other cannulas.

Lasers, electrocautery devices, and ultrasonic scalpels are often used during surgery to cut, cauterize, ablate, or vaporize tissues inside the abdomen. The application of the devices create "surgical smoke" in the distended cavity as an unintended though not unexpected byproduct. Surgical smoke generally refers to gases or aerosols that may contain toxins, particulate matter, irritants, viable cells and viruses, water vapor, and other undesirable contaminants. Inside the abdominal cavity, the surgical smoke present a health risk to the patient and complicates the surgical procedure. In particular, the surgical smoke may be absorbed by the patient through the pneumoperitoneum and will obscure the surgeon's visibility of the surgical field. Outside the patient, the smoke poses a health risk to the surgical personnel if not properly filtered.

There are a number of prior art devices for evacuating the surgical smoke from the cavity and filtering any gases discharged into the surgical room. Some of these prior art systems for smoke evacuation use a smoke filter in combination with an external source of vacuum used to draw the smoke laden insufflation gas from the surgical site through the filter. The source of vacuum may be provided by a wall outlet available in the surgical rooms or a dedicated machine capable of regulating the fluid flow rate though the filtration system. Smoke evacuation systems using a wall vacuum are unsuitable for most surgical applications because they require lengthy and obtrusive rubber hoses running from the patient and periodic intervention by the surgeon to balance the flow of insufflation gas pumped into or aspirated from the patient. The second class of smoke evacuation systems, including stand-alone and dedicated machines, requires a substantial capital investment to both purchase and maintain the equipment.

Still another category of prior art smoke evacuation systems includes strictly passive filtration systems that avoid the use of vacuum. U.S. Pat. No. 6,110,259 to Schultz and PCT application no. PCT/US99/28204 to Booth, which are both incorporated in their entirety by reference, operate solely in response to the pressure differential created by the surgical site and ambient air.

Schultz discloses a smoke filter and fluid conduit operatively coupled to a pressurized surgical site wherein the fluid flow rate is determined by the inherent properties of the filter media and the 'substantially unobstructed fluid flow path' through the fluid conduit. As an advantage, Schultz asserts that his invention eliminates the dependency on a vacuum source and combination of 'flow restrictors or reducers' and filters. Moreover, the Schultz smoke evacuation system consisting only of a filter and fluid conduit teaches away from the use of multiple, in-line structures (filters, resistors, etc.) for stepping or reducing suction whose presence would avoid the simplicity cited as an advantage.

Notwithstanding the fluid regulatory properties of the filter media, the Schultz smoke evacuation system requires a stopcock to start and stop the fluid flow through the system. The stopcock remains in the closed position prior and during the application of the laser, electrocautery device, or ultrasonic scalpels, thereby preventing the escape of any smoke from the surgical site. The stopcock is only opened after the surgical site becomes has saturated with smoke that visibility is impaired. The stopcock is then turned to the full open position, at which point the pneumoperitoneum is rapidly deflated and the surgical smoke passed through the filter. Prior to any further surgery, the stopcock is again closed and the pneumoperitoneum re-pressurized by insufflation device, which may take uncomfortably long period of time. The process of evacuating the smoke and reinflating the pneumoperitoneum may be repeated numerous times during the laparoscopic procedure.

A significant disadvantage of the Schultz system is that the ability of the surgeon to visualize the surgical site and proceed with surgery is significantly hampered during the period that the smoke is evacuated and the pneumoperitoneum distended again. Not only is it inconvenient, but is poses a risk to the patient. More specifically, the surgeon is prevented from observing or intervening on behalf of a patient that is experience internal hemorrhaging, for example, while repeatedly inflating and evacuating the pneumoperitoneum.

Booth discloses a flow control device interposed between the surgical site and the smoke evacuation filter. Although the character of the flow control device is unspecified it would appear to be a form of stopcock consistent with the mechanism shown by Schultz. As such, the Booth device suffers the same drawbacks as the Schultz invention.

SUMMARY

The present invention overcomes the limitations of the prior art with a fluid flow regulator which, when operatively integrated into a passive smoke evacuation system, regulates the flow rate to permit the continuous evacuation of surgical smoke without deflating the pressurized surgical site. The optimal evacuation flow rate, which is approximately 0.5 to 6.5 liters per minute, maintains the pneumoperitoneum in a distended position continuously through the duration of the laparoscopic procedure, permitting the surgical procedure to be conducted without interruption necessitated by deflation of the pneumoperitoneum used to smoke evacuation and subsequent reinflation.

The fluid flow regulator of the present invention is comprised of (i) a flow regulating means for providing a predetermined resistance to the flow of fluid, the appropriate resistance determined as a function of system variables including the resistance of the filtration system and (ii) at least one fluid conduit connecting means for coupling the flow regulating means to the smoke filtration system. The fluid flow regulator may be coupled to the downstream side of the smoke filtration system or, alternatively, between the filter and the surgical site.

In some embodiments, the flow regulating means is comprised of a diaphragm with at least one orifice of predetermined diameter, the diameter of the orifice restricting the flow of gas expelled from the surgical site within a range sufficient to effectively evacuate surgical smoke without deflating the pneumoperitoneum. The fluid flow regulator may be detachable from the smoke filtration system, thereby allowing one to select the flow regulator of appropriate resistance without replacing the filter itself. In other embodiments, the flow regulating means includes means for attaching a suction device to accelerate the evacuation of smoke when desirable.

In some embodiments, the orifice has an effective diameter of 0.5 to 5 millimeters, although this is subject to vary depending on the fluid flow resistance provided by the other components of the smoke evacuation system, namely the diameter of the cannula, the length and diameter of any conduits, and the resistance afforded by the filtration system itself.

In still other embodiments, the fluid flow regulator includes a system of flow regulating means which may include, for example, a plurality of differently sized orifices which may be operatively coupled to the filtration system to provide an optimal fluid flow independent of the system variables. The system variables that may influence the selection of the proper orifice include the pressure at the surgical site, the insufflation gas, the amount of smoke generated, the resistance provided by the various components of the evacuation system. In some embodiments, the plurality of orifices may be integrated into a single article of manufacture or apparatus to provide versatility and convenience to the surgeon.

The invention may also be characterized by a novel combination of steps. The method of using a fluid flow regulator in a minimally-invasive surgical procedure is comprised of the steps of (i) selecting the appropriate fluid flow regulator in consideration of the limitations described herein; (ii) operatively coupling the fluid flow regulator and smoke filtration system to a surgical site; (iii) pressurizing the surgical site with insufflation gas to distend the pneumoperitoneum; (iv) maintaining the distension of the pneumoperitoneum at a substantially constant position during the surgical procedure by simultaneously replenishing the surgical site with insufflation gas and continuously evacuating insufflation gas and/or surgical smoke through the smoke filtration system at a fluid flow rate substantially equal to the rate for replenishing the surgical site; and (v) evacuating the insufflation gas and surgical smoke at the conclusion of the minimally-invasive surgical procedure.

According to the method of the present invention, the fluid flow regulator may be used to limit or otherwise regulate the flow of fluid from the surgical site to fundamentally alter practice of laparoscopic surgery. In particular, application of the fluid flow regulator allows surgical smoke to be continuously evacuated from the surgical site without the need to interrupt the procedure to deflate the pneumoperitoneum and remove smoke. This additional step present in prior art systems prolongs the procedure and puts the patient at unnecessary risk for the period of time necessary to re-inflate and reestablish visual contact with the surgical site.

Therefore, the present invention reduces the risk to patients, reduces the time necessary to perform surgical procedures, reduces unnecessary manipulation of the smoke evacuation system as compared to prior art systems, namely Schultz and Booth. Also, the present invention provides a truly passive pressure maintenance system with little or no intervention or adjustment necessary by operating personnel.

DETAILED DESCRIPTION

The present invention pertains to a fluid flow regulator permitting which, when operatively coupled to a passive filtration system, provides an apparatus and method for optimizing the fluid flow rate evacuated from a laparoscopic surgical site, thereby permitting the continuous evacuation of surgical smoke without deflating the pressurized surgical site.

Figure 1:
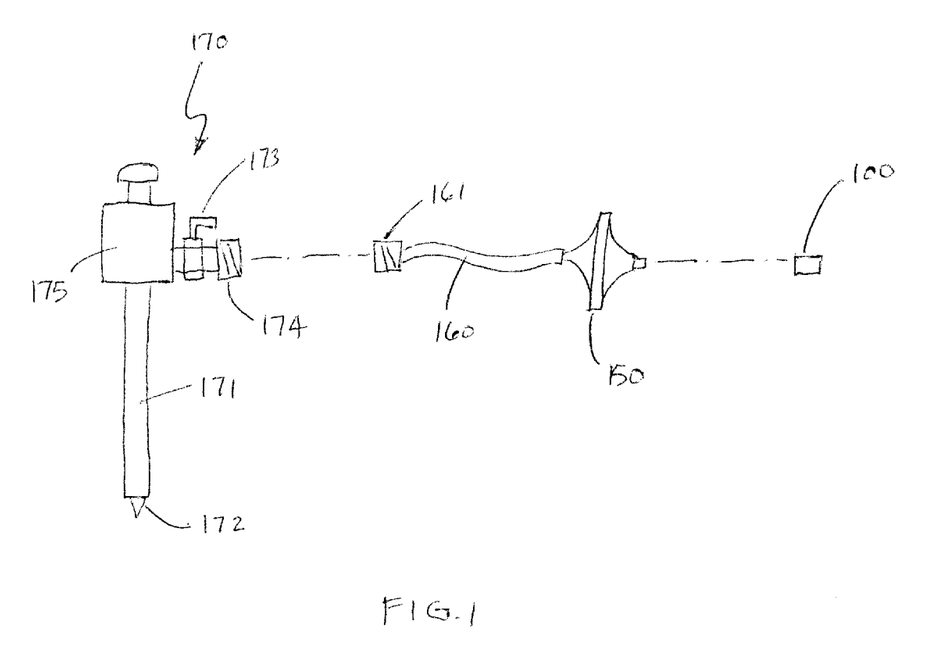
FIG. 1 is a schematic diagram of a smoke evacuation system of the present invention.

Referring to FIG. 1, a schematic diagram of a smoke evacuation system of the present invention is illustrated. The smoke evacuation system in this embodiment is comprised of a trocar assembly 170, a smoke filtration system 150, and a fluid flow regulator 100. In general, the trocar assembly 170 well known in the prior art is comprised of a cannula 171 with a removable faceted tip 172 for making a surgical incision, a stopcock 173, and a connector 174 for operationally coupling the insufflation device (not shown) to the surgical site. The trocar assembly 170 varies in size, shape, and configuration depending on the manufacturer and the functional requirements of the surgical procedure. Although commonly used, a direct fluid connection or Veress needle may be provided in place of the trocar assembly 170.

The smoke evacuation system also includes a smoke filtration system for filtering the various contaminates in the fluid aspirated from the surgical site. The smoke filtration system 150 includes a filter adapted to remove the surgical smoke including contaminates and water vapor present in the aspirated fluid. The filter 150 is adapted to be operably coupled to the surgical site and may include, for example, a flexible hose 160. The trocar assembly 170 and smoke filtration system 150 may be coupled by connectors 161 and 174 adapted to detachably engage one another. Suitable connectors include push-on type connectors, such as hose barbs, and screw-on type connectors, such as luer locks.

Figure 2:
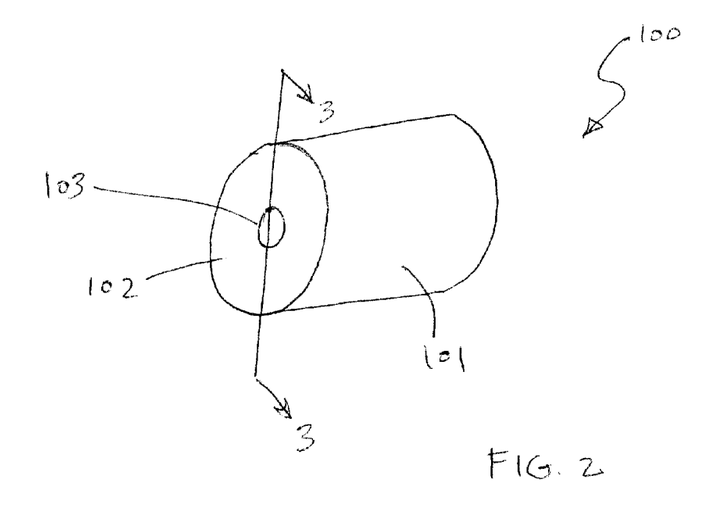
FIG. 2 is an isometric view of the fluid flow regulator of the first preferred embodiment of the present invention.
Figure 3:
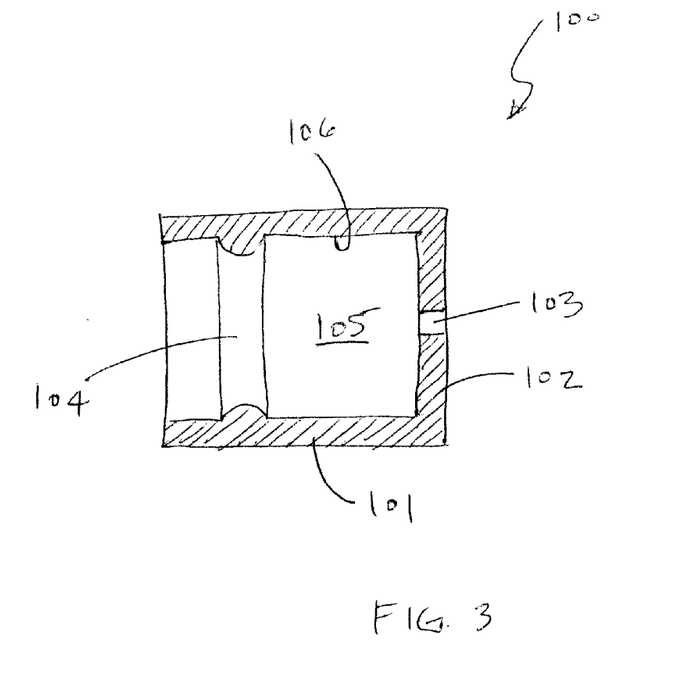
FIG. 3 is a cross-sectional view of the fluid flow regulator of the first preferred embodiment of the present invention.

Referring to FIGS. 2 and 3, the fluid flow regulator of the first preferred embodiment of the present invention is illustrated in an isometric view and cross section, respectively. The fluid flow regulator 100 is comprised of a flow regulating means, a housing 101, and a fluid conduit connecting means. The purpose of the flow regulating means is to provide a barrier that limits, without entirely stopping, the flow of fluid expelled from the smoke evacuation system. The flow regulating means in the preferred embodiment a diaphragm 102 with a substantially circular orifice 103 having a characteristic diameter. The orifice 103 is one of numerous features or constructions, which when combined with a substantially unobstructed fluid conduit (introduced below) coupled to the filter 150, offers a significant obstruction to the free flow of fluid through the filter. A significant obstruction is a deliberate impediment to the flow of fluid used to provide a pressure drop beyond that afforded by the unconstricted fluid conduit 160 that operatively couples the filter 150 to the surgical site.

The diameter of the orifice 103 of the this embodiment is subject to variation depending on pressure at the surgical site, the desired fluid flow rate through the smoke evacuation system, the pressure drop across the various components of the smoke evacuation system, as well as the insufflation gas. Preferably, the diameter ranges between 0.5 millimeters and 5 millimeters. One skilled in the art will recognize that the area of the orifice 103 will vary if a shape other than a circle is implemented.

The fluid conduit connecting means is a device for coupling the flow regulating means to smoke filtration system without any substantial loss of gas. In this embodiment, the flow regulating means includes a cylindrical-shaped housing 101 and boss 104 that protrudes from the inner surface 106, both of which are composed of an elastic material. As illustrated in cross section in FIG. 4, the housing 101 and boss 104 constitute the female end of a hose barb connection adapted to stretch over and frictionally engage a male hose barb connector. The elasticity of the conduit connecting means is determined in part by the material from which it is made. In the preferred embodiment, the conduit connecting means is manufactured from an elastomer, although one skilled in the art will recognize that a number of alternative materials would also be suitable with appropriate modification of the size and thickness of the structural elements. In the alternative, various connectors including push-on type connectors and threaded connections including luer locks may be adapted to couple the fluid flow regulator 100 to the smoke filter 150. On other embodiments, the fluid flow regulator 100 may be manufactured as an integral, non-detachable component of the filter 150.

Figure 4:
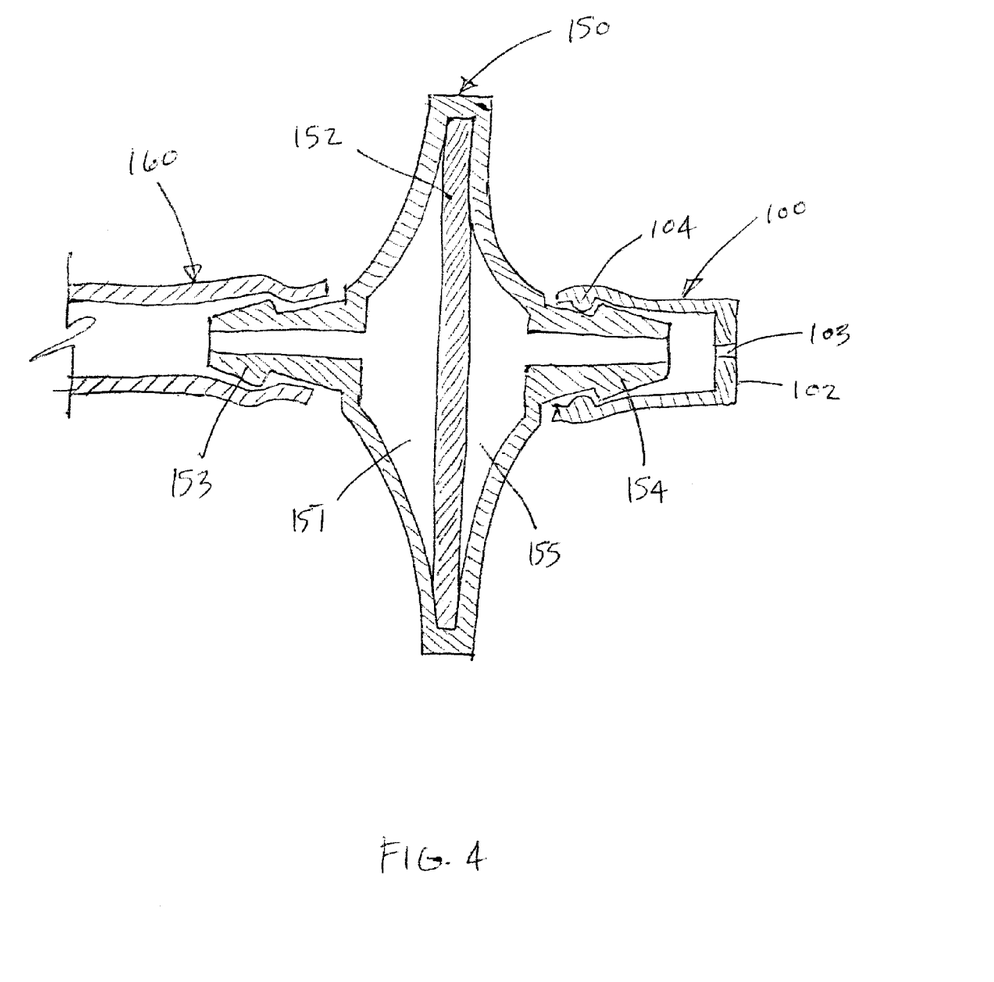
FIG. 4 is a cross-sectional view of the fluid flow regulator of the first preferred embodiment operatively coupled to a smoke evacuation filter.

In FIG. 4, the fluid flow regulator 100 is illustrated on the downstream side of the filter 150 where it is in fluid communication with the posterior filter chamber 155. On the opposite side of the filter media 152 is the anterior filter chamber 151 which is in fluid communication with the surgical site, either directly or indirectly by means of a conduit 160 and optional trocar assembly 170. In the alternative, a fluid flow regulator with appropriate modification may be inserted between the trocar assembly 170 and the smoke filtration system 150 with no loss of performance or function.

Figure 5:
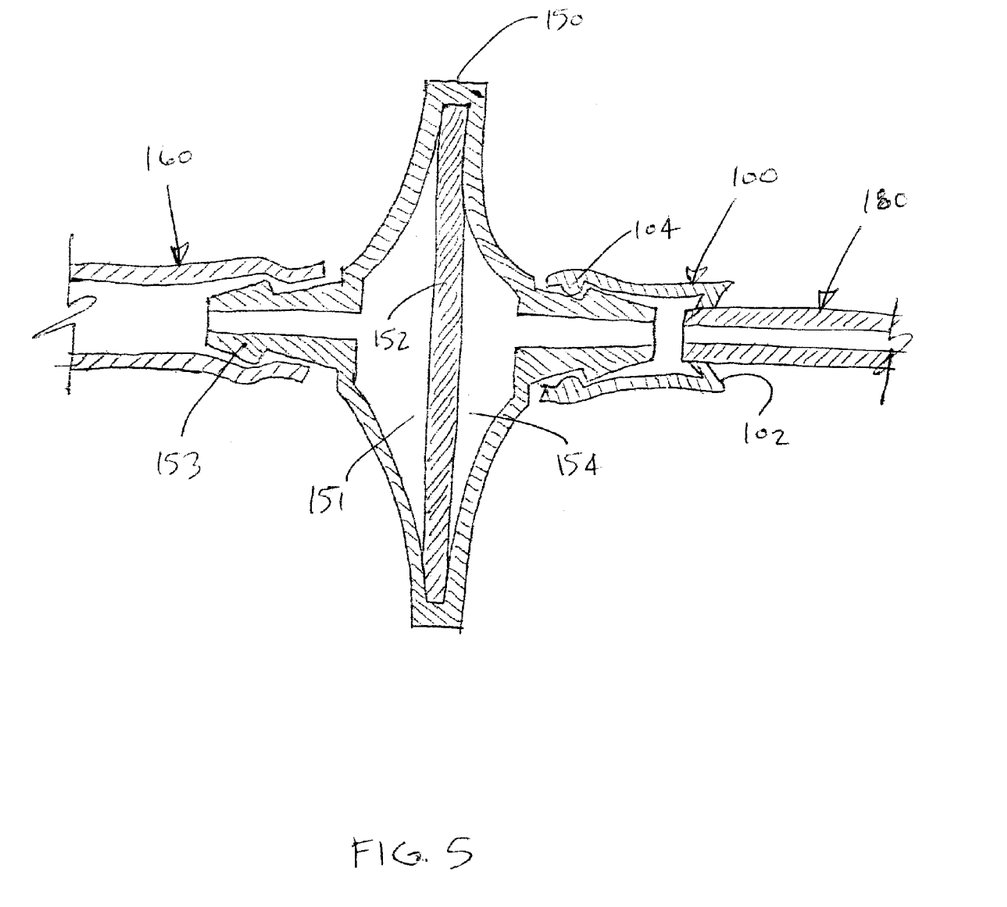
FIG. 5 is a cross-sectional view of the fluid flow regulator of the first preferred embodiment operatively coupled to a smoke evacuation filter and vacuum.

Referring to FIG. 5, a cross-sectional view of the fluid flow regulator of the first preferred embodiment operatively coupled to a smoke evacuation filter and vacuum is illustrated. Here, the diaphragm 102 is made of an elastic material permitting the orifice 103 to stretch and engage a source of vacuum 180. An elastic diaphragm has the advantage of allowing the surgeon to temporarily attach and then disengage the vacuum 180 to accelerate the removal of surgical smoke or deflation of the pneumoperitoneum. The vacuum source 180 may ultimately be derived from a wall outlet and may be a cannular type device with manually operated values for controlling the application of negative pressure. In the alternative, the vacuum source 180 may be a pump programmed to apply vacuum automatically or under the control determined by the surgical staff.

According to the present invention, an individual fluid flow regulator 100 is one element of a system comprising a plurality of individual fluid flow regulators, each fluid flow regulator providing a different fluid flow resistance for a given pressure differential or flow rate. In the present embodiment, the variation in fluid flow resistance is achieved by varying the diameter of the orifice 103 between the individual fluid flow regulators. For example, system may comprise three fluid flow regulators having orifice diameters of 0.5, 1.0, and 2.0 millimeters. In general, one of the plurality of fluid flow regulators will provide an optimal fluid flow rate in consideration of the pressure at the surgical site, the fluid resistance present by the entire smoke evacuation system, the desired fluid flow rate through the smoke evacuation system, and to a lesser degree, the particular insufflation gas.

By way of example, an obese patient may require a higher surgical site pressure which would give rise to a high fluid flow rate through the filter if not compensated. A flow regulator with a relatively high resistance, i.e. the smallest diameter orifice, would be required to increase the overall resistance of the smoke filtration system reduce or otherwise limit the fluid flow through the system. On the other hand, a relatively thin patient may require a relatively low surgical site pressure, which would give rise to a low fluid flow rate through filter all things being equal. A flow regulator with a relatively low resistance, i.e. the largest diameter orifice, would be required to hold the overall resistance of the smoke filtration system low and so as not to further impede the fluid flow through the system.

Figure 6:
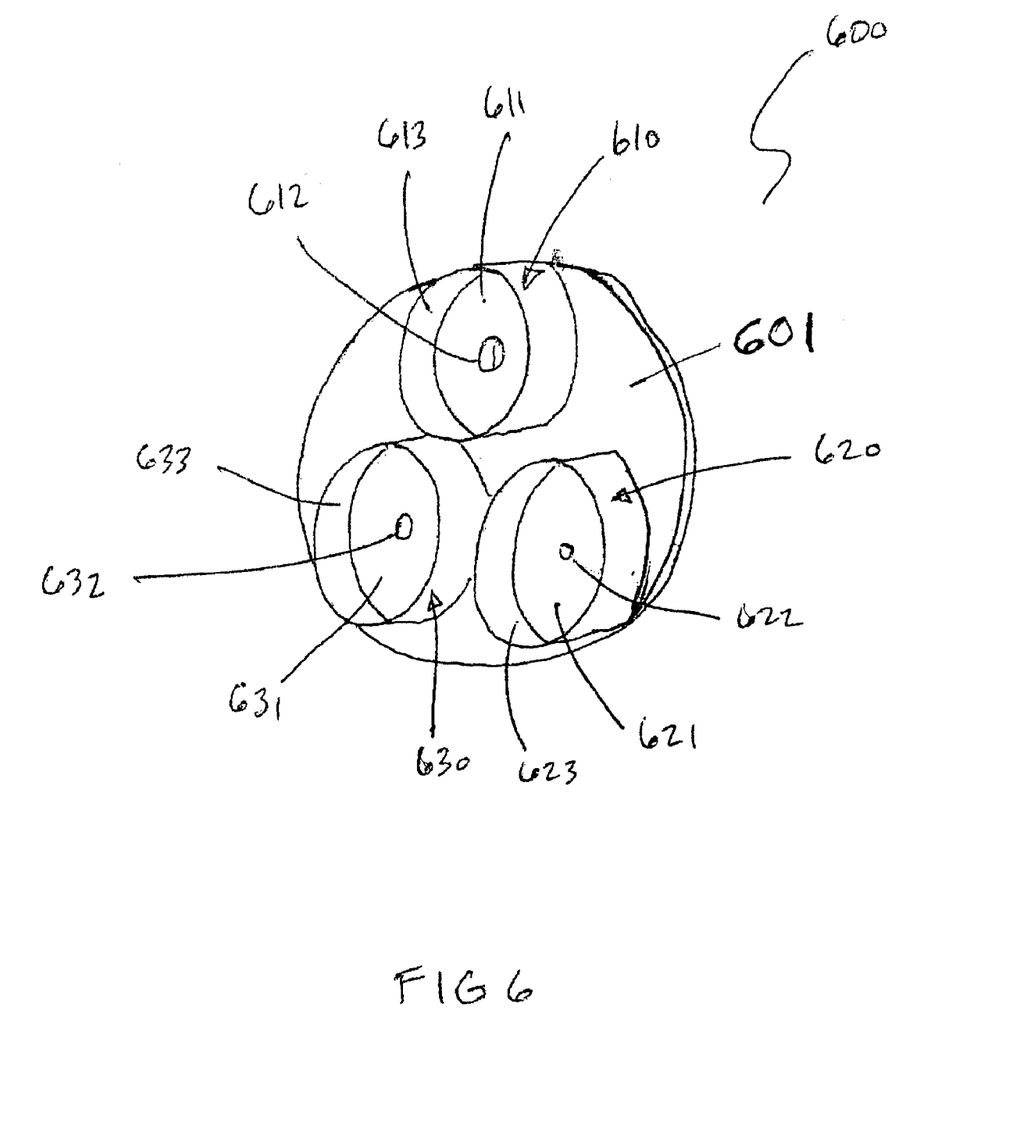
FIG. 6 is an isometric view of the fluid flow regulator of the second preferred embodiment of the present invention.

Referring to FIG. 6, an isometric view of the fluid flow regulator of the second preferred embodiment of the present invention is illustrated. The flow regulating system 600 is comprised of a plurality of independently operable fluid flow regulating units consistent with that described in the first preferred embodiment. Here, there are three individual flow regulating units 610, 620, 630. The units are comprised of substantially identical housings 613, 623, 633, each housing having a corresponding fluid flow regulating means comprised in this embodiment of a diaphragm 611, 621, 631 with a unique orifice 612, 622, 632. The housings 613, 623, 633 further include one of a variety of conduit connecting means as described above. The attaching means 601 affixes the plurality of flow regulating units together, thus providing a simple and cost effective device for regulating the flow through the filter 150 which if necessary may be rapidly and conveniently detached from a smoke filtering system and reattached at a different unit to provide a different fluid flow resistance.

According to the present invention, the fluid flow resistance provided by each of the plurality of flow regulating units is different from the other units. The fluid flow resistance provided by each unit, as determined by the corresponding orifice, is specifically configured to regulate the fluid flow through the smoke evacuation system for a set of pre-determined or "a priori" system variables, including but not limited to the desired surgical site pressure, desired fluid flow rate, resistance of the individual elements of the smoke evacuation system, and particular insufflation gas. The minimum and maximum flow resistance provided by the flow regulating system preferably corresponds to the minimum and maximum pressure drop necessary to achieve a desired fluid flow rate as a function of the system variables introduced above. The resistance of the intermediate units is, preferably, selected to provide incremental differences in resistance in approximately equal units scaled between the maximum and minimum resistance.

The desired surgical site pressure, being a function of the patient weight, may be estimated in advance of the laparoscopic procedure. The desired flow rate may also be predetermined and will depend to some degree on the surgical device use and the tissue to be treated. For example, the ablation of fatty tissue with a laser creates a relatively large amount of smoke and would dictate a relatively high fluid flow rate. These and other variables may be charted against the fluid flow resistance of the smoke evacuation system. A chart or look-up-table may be generated to provide a simple and convenient way for the surgeon to estimate the appropriate unit of the plurality of flow regulating units 610, 620, 630 to operatively couple to the smoking filtrations system to achieve the desired flow rate. This invention, therefore, provides a means to accurately "tune in" the optimal fluid flow resistance based upon a priori knowledge of the system variable without the need to swap the filter as Schultz would suggest.

Figure 7:
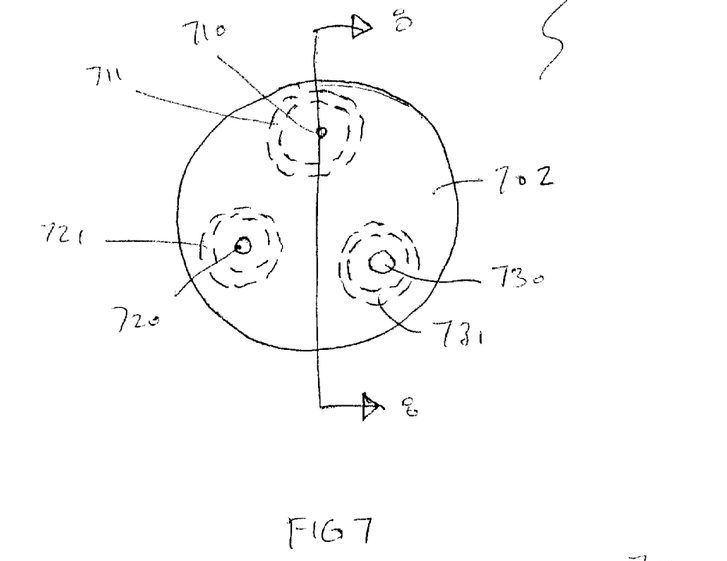
FIG. 7 is a plan view of the fluid flow regulator of the third preferred embodiment of the present invention.

Referring to FIG. 7, a plan view of the fluid flow regulator of the third preferred embodiment of the present invention is illustrated. The fluid flow regulator 700 is comprised of a fluid conduit connecting means 703 and a plurality of flow regulating means for providing a predetermined resistance to the flow of fluid. The conduit connecting means 703 is comprised in this embodiment of an elastic housing 705 and boss 704 that protrude from the interior face of the housing 705 to engage the hose barb of a filtration system. The conduit connecting means 703, which may operate identically to the conduit connecting means of the first preferred embodiment, holds the fluid flow regulator and the primary orifice 706 of the first disk 701 in operational engagement to the smoke filtration system. Alternative conduit connecting means discussed above would also be suitable if properly adapted to couple with the filtration system.

Figure 8:
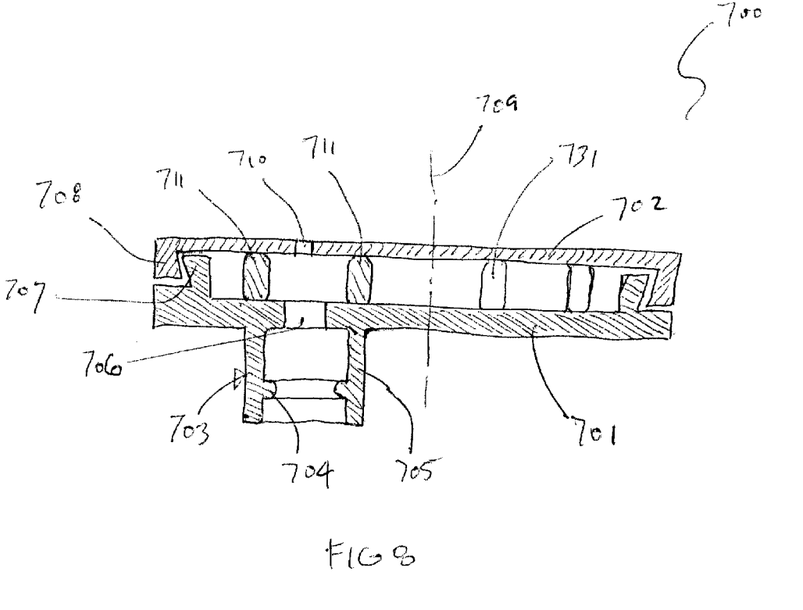
FIG. 8 is a cross-sectional view of the fluid flow regulator of the third preferred embodiment of the present invention.

The flow regulating means, in general, may be comprised of the plurality of isolated secondary orifices, each secondary orifice providing a different fluid flow restriction. In this embodiment, the flow regulating means is comprised of three secondary orifices 710, 720, 730 that populate a second disk 702. Each of the three orifices is isolated from the other two orifices by means of the O-rings 711, 721, 731 that substantially prohibit the fluid flow from escaping by means other than the intended secondary orifice. The secondary orifice coinciding with the primary orifice 706 is in fluid communication with the filtration system. In particular, orifice 710 as illustrated is in fluid communication with the primary orifice 706 and the surgical site indirectly. Only one of the secondary orifices is in fluid communication with the filtration system at any given time.

To the claim of this embodiment, the secondary orifice in communication with the primary orifice 706 may be changed by rotating the second disk 702 relative to the first disk 701 about the axis 709 until a difference secondary orifice is aligned with the primary orifice 706. The first and second disks 701, 702 are held in slidable engagement by means of the first and second mating edges 707 and 708.

The three orifices 710, 720, 730 illustrated in this embodiment have diameters chosen to regulate the fluid flow through the smoke evacuation system for a set of predetermined set of system variables, including but not limited to the desired surgical site pressure, desired fluid flow rate, pressure drop across the individual elements of the smoke evacuation system, and particular insufflation gas. The minimum and maximum flow resistance provided by the flow regulating system preferably corresponds to the minimum and maximum pressure drop necessary to achieve a desired fluid flow rate as a function of the system variables introduced above. The resistance of the intermediate units is, preferably, selected to provide incremental differences in resistance in approximately equal units scaled between the maximum and minimum resistance. Representative orifices diameters may be 0.5, 1.0, and 2.0 millimeters.

In an alternative version of the third embodiment, the fluid flow regulating means may comprise a system of smaller, more restrictive orifices than that provided by the three orifices 710, 720, 730. Equivalent fluid flow resistance may be achieved by using a plurality of smaller diameter orifices that conduct fluid through the secondary disk 702. The plurality of "petite" orifices, if confined to the region in the interior space defined by the corresponding O-ring, may collectively provide the same flow resistance and therefore fluid flow as an individual orifice represent by orifices 710, 720, 730, for example.

In a fourth preferred embodiment, the fluid flow regulator is comprised of variable fluid flow regulating means and a fluid conduit connecting means for operatively engaging the variable fluid flow regulating means to the smoke filtration system. The purpose of the variable fluid flow regulating means is to provide variable fluid flow resistance for use in concert a passive smoke evacuation system.

The design of the variable fluid flow regulating means may be based upon known gas value systems. The critical difference between the variable fluid flow regulating means and the prior art is the presence of flow restriction indicia in proximity to the knob, lever, or tuning device for adjusting the resistance of the valve. The flow restriction indicia are distinctive markings, not unlike calibration markings, on the variable fluid flow regulating means that are proportional or otherwise quantitatively related to the fluid flow resistance provided by the variable fluid flow regulating means. The flow restriction indicia may be used with a priori knowledge of the system variables to "predetermine" or otherwise "pre-set" the appropriate variable fluid flow regulating means necessary to achieve the optimum fluid flow rate through the smoke evacuation system.

The optimum fluid flow rate is within a range sufficient to maintain the pneumoperitoneum in a distended position without deflation. According to the present invention, the optimum fluid flow rate may be maintained throughout the surgical procedure without interruption. Proper selection of the fluid flow resistance permits a surgeon to perform the surgical procedure with the trocar assembly stopcock 173 in the full-on position through the entire surgical procedure without intervention or periodic cycling required in prior art systems.

The a priori information includes but is not limited to the desired surgical site pressure, desired fluid flow rate, pressure drop across the individual elements of the smoke evacuation system, and particular insufflation gas. This information may be charted against the fluid flow resistance of the smoke evacuation system, including the smoke filtration system and trocar assembly, to predetermine the optimal setting for the variable fluid flow regulating means. A chart or look-up-table, LOC, may be generated to provide a simple and convenient way for the surgeon to estimate the appropriate unit of the plurality of units in the flow regulating system to operatively couple to the smoking filtrations system.

Figure 9:
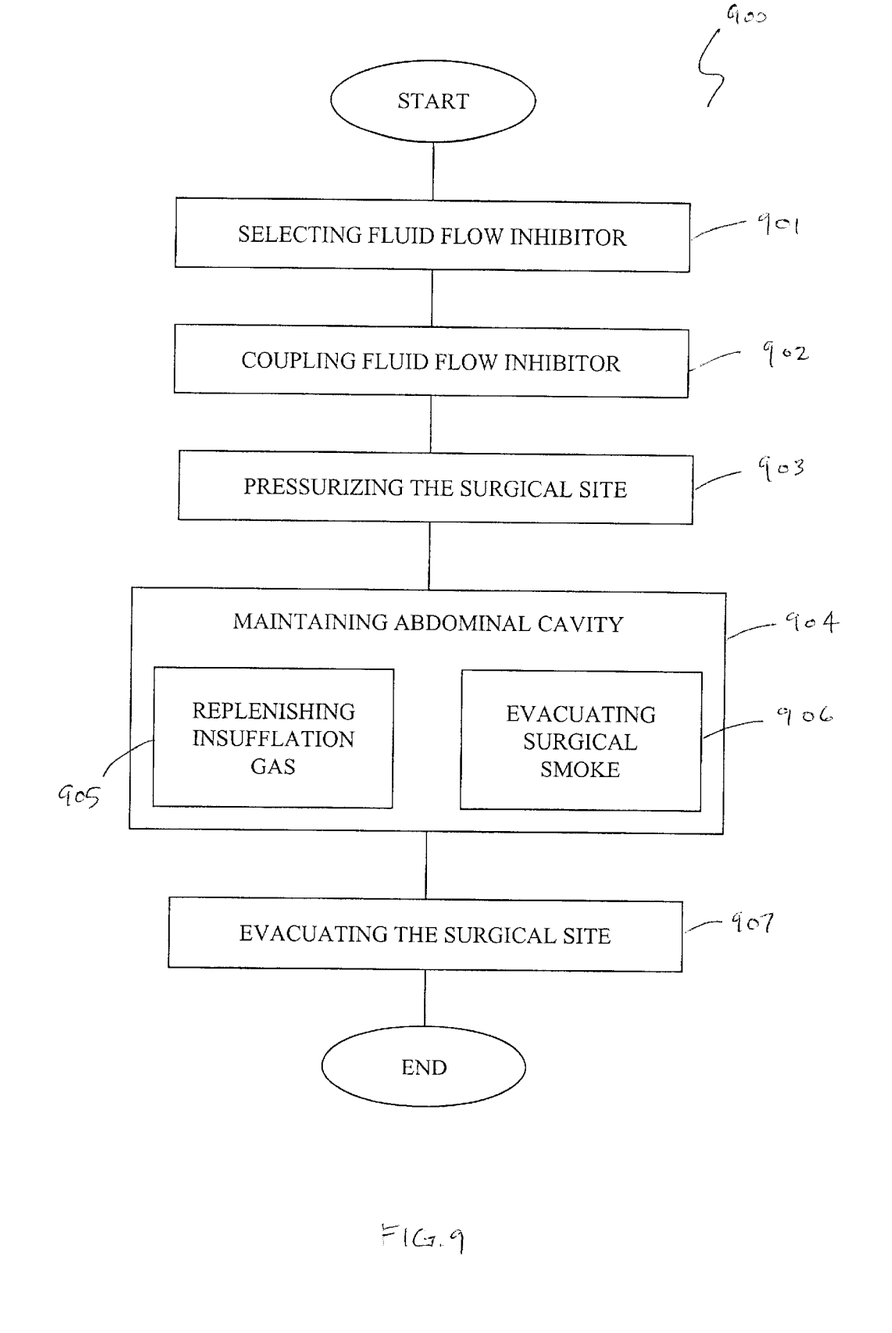
FIG. 9 is a flow chart of the method of using the fluid flow regulator of the present invention.

Referring to flow chart of FIG. 9, another aspect of the present invention is the novel method of use of a fluid flow regulator to regulate the flow of fluid in a passive smoke evacuation system. The method of using the fluid flow regulator of the present invention preferably pertains to various minimally invasive surgical procedures and is comprised of the steps described below.

The first step 901 is to select a fluid flow regulator which, when operatively coupled to a smoke filtration system and the pressurized surgical site restricts the flow of fluid from the surgical site at a rate less than the maximum rate at which the insufflation device can replenish the gas. Although many modem insufflation devices can supply insufflation gas at a rate of 16 to 25 liters per minute, this rate may be excessive and lead to the dehydration and cooling of the patient. Preferably, the flow regulator in combination with the smoke filtration system and trocar assembly 170 gives rise to a fluid flow rate of between 1 and 6.5 liters per minute through the smoke filtration system. Although some embodiments of the present invention are adapted to receive a source of vacuum, the preferable fluid flow rate is that fluid flow rate induced as a result of the pressure differential arising from the pressurized surgical site and the ambient air alone.

In the case of the variable fluid flow regulating means described in the fourth embodiment, for example, the first step 901 implicitly includes the selection of the proper fluid flow setting predetermined that results in the optimal fluid flow rate.

The second step 902 is to operatively couple the fluid flow regulator selected in the previous step 901 and smoke filtration system to a surgical site. The fluid flow regulator is operatively coupled when connected in such a manner as to permit the discharge of fluid from the surgical site through the smoke filtration system. The connection may include a trocar assembly or, in the alternative, a direct connection provided by a Vereese needle, for example. The stopcock 173 on the trocar assembly 170 is preferably set to the closed position prior to achieving the maintenance pressure necessary to distend the abdominal cavity.

The third step 903 involves the pressurization of the surgical site with insufflation gas to distend the pneumoperitoneum. The distention should be sufficient to create a cavity large enough to permit the entry and utilization of laparoscopic and endoscopic instruments. The pressurization step 903 may occur prior to or simultaneously with the prior two steps 901, 902.

The fourth step 904 is to maintain the distension of the pneumoperitoneum at a substantially constant position throughout the surgical procedure. According to the present invention, the distention of the pneumoperitoneum may be achieved by simultaneously replenishing the insufflation gas and evacuating the insufflation gas/surgical smoke at the surgical site. The step of replenishing 905 the surgical site with insufflation gas is performed by the insufflation device, which is preferably programmed to supply the gas at a constant rate. For safety reasons, the rate at which the device supplies gas may automatically drop below the maximum level when a maximum pressure is achieved. Concurrent with the replenishment of insufflation gas, the smoke evacuation system continuously evacuates 906 insufflation gas or a combination of insufflation gas and surgical smoke through the smoke filtration system.

According to the present invention, the resistance of the flow regulator 100 is selected such that the fluid flow rate evacuated is substantially equal to the rate at which insufflation gas is supplied to the surgical site in the replenishing step 905. One skilled in the art will recognize that the flow rate generated by the insufflation device will vary over time depending on the maximum surgical site pressure. Moreover, the fluid flow rate out of the smoke evacuation system will vary some depending on any variation of the pressure at the surgical site. That being said, proper selection of the resistance of the fluid flow regulator 100 will give rise to an average flow rate out of the surgical site that is substantially equal to the average flow rate into the surgical site, less any losses due to leakage through the surgical instruments, for example.

According to the present invention, the proper selection of the fluid flow regulator 100 permits surgical smoke to be evacuated by "bleeding off" gas at the same time the gas is replenished and the surgical smoke generated, thereby by obviating the need to completely deflate the pneumoperitoneum of surgical smoke as was done in prior art systems, namely the Schultz and Booth smoke evacuation systems. This invention therefore allows the surgeon the ability to continue the surgical procedure without interruption during and after the application of a laser, electrocautery devices, or ultrasonic scalpels.

In the last step 907, the pneumoperitoneum is allowed to deflate and the insufflation gas and any residual surgical smoke evacuated at the conclusion of the minimally-invasive surgical procedure. Here, the pneumoperitoneum need be deflated only once, unlike the prior art procedures in which the pneumoperitoneum was deflated each time the visibility in the abdomen became obstructed by the accumulation of surgical smoke.

Although the above description contains many specifics, these should not be construed as limiting the scope of the invention, but rather as merely providing illustrations of some of the presently preferred embodiments of this invention.

Therefore, the invention has been disclosed by way of example and not limitation, and reference should be made to the following claims to determine the scope of the present invention.

I claim:

1. A fluid flow regulator, for a passive smoke evacuation system including a smoke filtration system, the flow regulator comprising:
    (a) a flow regulating means for providing a predetermined resistance to the flow of fluid, the resistance determined as a function of system variables including the resistance of the filtration system;
    (b) at least one fluid conduit connecting means for coupling the flow regulating means to the smoke filtration system;
    (c) wherein the fluid flow rate through the smoke evacuation system induced by a pressurized surgical site is limited to a range sufficient to substantially evacuate surgical smoke without depressurizing the surgical site, and;
    (d) wherein the flow regulating means is comprised of a diaphragm with at least one orifice having a characteristic diameter for providing a significant obstruction to the flow of fluid.

2. The fluid flow regulator of claim 1, wherein at least one fluid conduit connecting means is a detachable coupling permitting the fluid flow regulator to engage and disengage the smoke evacuation system.

3. The fluid flow regulator of claim 2, wherein the diaphragm and at least one orifice of the flow regulating means is adapted to receive a suction device.

4. The fluid flow regulator of claim 1, wherein the fluid flow regulator is adapted to indirectly couple to the pressurized surgical site by means of the smoke filtration system.

5. The fluid flow regulator of claim 1, wherein the diameter of at least one orifice is between 0.5 and 5 millimeters.

6. The fluid flow regulator of claim 5, wherein the diameter of the orifice is substantially equal to 1.1 millimeters.

7. The fluid flow regulator of claim 5, wherein the flow regulator consists of one orifice of predetermined diameter.

8. The fluid flow regulator of claim 1, wherein the flow regulator is comprised of a plurality of orifices of different diameters each providing different fluid flow resistances.

9. The fluid flow regulator of claim 8, wherein any single orifice among the plurality of orifices which are physically attached to one another may be isolated so as to prevent gas expelled from the pressurized surgical site to pass through more than one orifice at a time.

10. A fluid flow regulator, for a passive smoke evacuation system including a smoke filtration system, the flow regulator comprising:
    (a) a flow regulating means for providing a predetermined resistance to the flow of fluid, the resistance determined as a function of system variables including the resistance of the filtration system; and
    (b) at least one fluid conduit connecting means for coupling the flow regulating means to the smoke filtration system;
    (c) wherein the fluid flow rate through the smoke evacuation system induced by a pressurized surgical site is limited to a range sufficient to substantially evacuate surgical smoke without depressurizing the surgical site, and;
    (d) wherein the flow regulating means is variable and capable of adjustment to affect a variable fluid flow resistance for the smoke evacuation system; the flow regulating means including indicia for quantitatively identifying the fluid flow resistance being applied by the flow regulating means.

11. A method of using a fluid flow regulator in a minimally-invasive surgical procedure; the fluid flow regulator comprising a flow regulating means for providing a significant obstruction to the flow of fluid and at least one fluid conduit connecting means for coupling the flow regulating means to a passive smoke filtration system; the method comprising the steps of:
    (a) selecting a fluid flow regulator which, when operatively coupled to the passive smoke filtration system and a pressurized surgical site restricts the flow of fluid from the surgical site at a rate less than that provided by an insulation device in the maintenance mode;
    (b) operatively coupling the fluid flow regulator and smoke filtration system to the surgical site;
    (c) pressurizing the surgical site with an insufflation gas to distend the pneumoperitoneum, thereby creating a cavity sufficiently large to permit the entry and utilization of laparoscopic and endoscopic instruments;
    (d) maintaining the distension of the pneumoperitoneum at a substantially constant position while simultaneously:
        (i) replenishing the pressurized surgical site with insufflation gas at a constant rate subject to a maximum surgical site pressure;
        (ii) continuously evacuating (a) insulation gas or (b) insulation gas and surgical smoke through the smoke filtration system at a fluid flow rate substantially equal to the rate for replenishing the surgical site;
    (e) evacuating the insufflation gas and surgical smoke at the conclusion of the minimally-invasive surgical procedure.

12. The method of using a fluid flow regulator in a minimally-invasive surgical procedure of claim 11, wherein the flow regulating means is comprised of a diaphragm with at least one orifice of predetermined diameter.

13. The method of using a fluid flow regulator in a minimally-invasive surgical procedure of claim 12, wherein the fluid conduit connecting means is a detachable coupling permitting the fluid flow regulator to engage and disengage the smoke evacuation system, wherein the fluid flow rate through the smoke filtration system may be altered in a predetermined manner in the course of a surgical procedure without replacing the smoke filtration system.

14. The method of using a fluid flow regulator in a minimally-invasive surgical procedure of claim 13, wherein the diaphragm and at least one orifice of the fluid conduit connecting means are adapted to receive a suction device.

15. The method of using a fluid flow regulator in a minimally-invasive surgical procedure of claim 12, wherein the smoke filtration system is positioned between the pressurized surgical site and the fluid flow regulator.

16. The method of using a fluid flow regulator in a minimally-invasive surgical procedure of claim 12, wherein the diameter of at least one orifice is between 0.5 and 5 millimeters.

17. The method of using a fluid flow regulator in a minimally-invasive surgical procedure of claim 16, wherein the predetermined diameter of the orifice is substantially equal to 1.1 millimeters.

18. The method of using a fluid flow regulator in a minimally-invasive surgical procedure of claim 16, wherein the flow regulator consists of one orifice of predetermined diameter.

19. The method of using a fluid flow regulator in a minimally-invasive surgical procedure of claim 12, wherein the flow regulator is comprised of a plurality of orifices of different diameters capable of providing different fluid flow resistances.

20. A method of using a variable fluid flow regulating means with a passive smoke filtration system in a minimally-invasive surgical procedure; the variable fluid flow regulating means including flow restriction indicia quantitatively related to the fluid flow resistance of the variable fluid flow regulating means; the method comprising the steps of:

(a) setting the variable fluid flow regulating means such that, when operatively coupled to the smoke filtration system and a pressurized surgical site, restricts the flow of fluid from the surgical site at a rate less than 6.5 liters per minute;

(b) operatively coupling the variable fluid flow regulating means and smoke filtration system to a surgical site;

(c) pressurizing the surgical site with an insufflation gas to distend the pneumoperitoneum, thereby creating a cavity sufficiently large to permit the entry and utilization of laparoscopic and endoscopic instruments;

(d) maintaining the distension of the pneumoperitoneum at a substantially constant position while simultaneously:

(i) replenishing the pressurized surgical site with insufflation gas at a constant rate subject to a maximum surgical site pressure;

(ii) continuously evacuating (a) insufflation gas or (b) insufflation gas and surgical smoke through the smoke filtration system at a fluid flow rate substantially equal to the rate for replenishing the surgical site;

(e) evacuating the insufflation gas and surgical smoke at the conclusion of the minimally-invasive surgical procedure.

* * * * *